US012426797B2

(12) United States Patent
Liu et al.

(10) Patent No.: US 12,426,797 B2
(45) Date of Patent: *Sep. 30, 2025

(54) SYSTEMS AND METHODS FOR SIMULTANEOUS MULTI-SLICE MULTITASKING IMAGING

(71) Applicant: SHANGHAI UNITED IMAGING HEALTHCARE CO., LTD., Shanghai (CN)

(72) Inventors: Qi Liu, Houston, TX (US); Yuan Zheng, Houston, TX (US); Jingyuan Lyu, Houston, TX (US); Zhongqi Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/662,991

(22) Filed: May 13, 2024

(65) Prior Publication Data
US 2024/0293040 A1 Sep. 5, 2024

Related U.S. Application Data

(63) Continuation of application No. 17/246,545, filed on Apr. 30, 2021, now Pat. No. 11,980,457.

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0044* (2013.01); *G01R 33/4835* (2013.01);
(Continued)

(58) Field of Classification Search
CPC . A61B 5/055; A61B 5/0044; A61B 2576/023; G01R 33/4835; G01R 33/543; G01R 33/5608; G06T 11/005
See application file for complete search history.

(56) References Cited

U.S. PATENT DOCUMENTS 8,583,213 B2 * 11/2013 Dumoulin ............... A61B 5/055
600/420
8,855,742 B2 * 10/2014 Foo .......................... A61B 5/062
600/417
(Continued)

FOREIGN PATENT DOCUMENTS

CN 108229066 A 6/2018

OTHER PUBLICATIONS

Jaime L. Shaw et al., Free-breathing, Non-ECG, Continuous Myocardial T1 Mapping with Cardiovascular Magnetic Resonance Multitasking, Magnetic Resonance in Medicine, 2019, 14 pages.
(Continued)

Primary Examiner — Gregory M Desire
(74) Attorney, Agent, or Firm — METIS IP LLC

(57) ABSTRACT

The present disclosure provides a system for MRI. The system may obtain a plurality of auxiliary signals and a plurality of imaging signals collected by applying an MRI pulse sequence simultaneously to a plurality of slice locations of a subject. For each of at least one target slice location of the plurality of slice locations, the system may generate at least one target image of the target slice location based on the plurality of auxiliary signals and the plurality of imaging signals. During the application of the MRI pulse sequence, phase modulation may be applied to at least one of the plurality of slice locations so that the plurality of slice locations have different phases during the readout of at least one of the plurality of imaging signals.

20 Claims, 9 Drawing Sheets

(51) Int. Cl.
*G01R 33/483* (2006.01)
*G01R 33/54* (2006.01)
*G01R 33/56* (2006.01)
*G06T 11/00* (2006.01)

(52) U.S. Cl.
CPC ....... *G01R 33/543* (2013.01); *G01R 33/5608* (2013.01); *G06T 11/005* (2013.01); *A61B 2576/023* (2013.01)

(56) References Cited

U.S. PATENT DOCUMENTS

| | | | |
|---|---|---|---|
| 9,254,112 B2* | 2/2016 | Tryggestad | G01R 33/5673 |
| 9,396,562 B2* | 7/2016 | Lefebvre | G01R 33/5611 |
| 9,414,766 B2* | 8/2016 | Jesmanowicz | A61B 5/055 |
| 9,462,961 B2* | 10/2016 | Furudate | A61B 5/743 |
| 9,482,732 B2* | 11/2016 | Chesneau | G01R 33/56509 |
| 9,797,970 B2* | 10/2017 | Zhou | G01R 33/4836 |
| 9,841,481 B2* | 12/2017 | Kerr | G01R 33/5611 |
| 10,139,465 B2 | 11/2018 | Setsompop et al. | |
| 10,436,866 B2 | 10/2019 | Bilgic et al. | |
| 10,436,871 B2* | 10/2019 | Li | G06V 10/25 |
| 10,459,055 B2* | 10/2019 | Griswold | G01R 33/4835 |
| 10,684,337 B2 | 6/2020 | Wu et al. | |
| 10,712,418 B2 | 7/2020 | Koch et al. | |
| 10,753,994 B2 | 8/2020 | Salerno et al. | |
| 11,517,198 B2* | 12/2022 | Ferrazzi | G01R 33/567 |
| 2012/0245453 A1 | 9/2012 | Tryggestad et al. | |
| 2016/0018499 A1 | 1/2016 | Bornert et al. | |
| 2020/0088822 A1 | 3/2020 | Jurrissen et al. | |
| 2020/0256939 A1 | 8/2020 | Wang | |
| 2020/0300951 A1 | 9/2020 | Ye et al. | |
| 2021/0116527 A1 | 4/2021 | Zheng et al. | |

OTHER PUBLICATIONS

Anthony G. Christodoulou et al., Magnetic Resonance Multitasking for Motion-resolved Quantitative Cardiovascular Imaging, Nature Biomedical Engineering, 2018, 12 pages.

Liu, Qi et al., Multiband Multitasking for Cardiac T1 Mapping, ISMRM & SMRT Annual Meeting & Exhibition an Online Experience, 2021, 4 pages.

First Office Action in Chinese Application No. 202111077794.8 mailed on Jan. 27, 2025, 15 pages.

Su, Shi et al., Preliminary Research on Controlled Aliasing in Parallel Imaging Results in Higher Acceleration, Journal of Integration Technology, 5(3): 84-90, 2016.

* cited by examiner

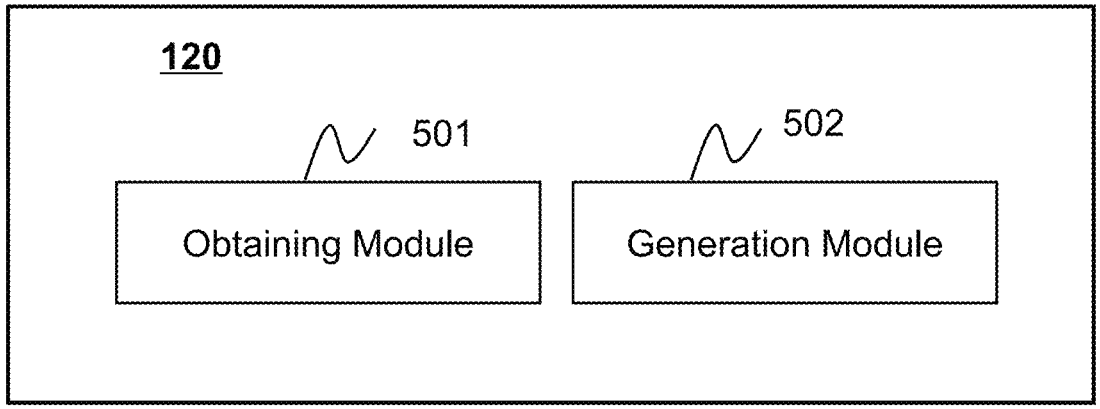

| Obtaining a plurality of auxiliary signals and a plurality of imaging signals, which are collected by applying an MRI pulse sequence simultaneously to a plurality of slice locations of a subject | 601 |

↓

| For each of one or more target slice locations of the plurality of slice locations, generating, based on the plurality of auxiliary signals and the plurality of imaging signals, one or more target images of the target slice location | 602 |

| Determining, based on the plurality of auxiliary signals, one or more temporal basis functions relating to one or more time-varying dimensions of a target slice location | 1001 |

↓

| Determining, based on the temporal basis function(s) and the plurality of imaging signals, one or more spatial basis functions relating to one or more spatial-varying dimensions of the target slice location | 1002 |

↓

| Generating, based on the temporal basis function(s) and the spatial basis function(s), one or more target images of the target slice location | 1003 |

FIG. 10

SYSTEMS AND METHODS FOR SIMULTANEOUS MULTI-SLICE MULTITASKING IMAGING

CROSS-REFERENCE TO RELATED APPLICATIONS

This application is a continuation of U.S. patent application Ser. No. 17/246,545, filed on Apr. 30, 2021, the contents of which are hereby incorporated by reference.

TECHNICAL FIELD

The present disclosure generally relates to magnetic resonance imaging (MRI), and more particularly, relates to systems and methods for MRI that combines simultaneous multi-slice (SMS) technique and multitasking technique (or referred to as SMS multitasking imaging herein).

BACKGROUND

Recently, SMS technique and multitasking technique have been used in MRI. The SMS technique allows an excitation of a plurality of slice locations of a subject (e.g., a patient) at the same time and can accelerate the scanning process. The multitasking technique is capable of acquiring MRI data of multiple dimensions (e.g., information relating to various physiological motions, relaxations, etc.) in a single MRI scan. Therefore, it is desirable to provide systems and methods for SMS multitasking imaging that combines the SMS technique and the multitasking technique, thereby achieving the advantages of both the multitasking technique and the SMS technique.

SUMMARY

According to one aspect of the present disclosure, a system for MRI is provided. The system may include at least one storage device including a set of instructions, and at least one processor configured to communicate with the at least one storage device. When executing the set of instructions, the at least one processor may be configured to direct the system to obtain a plurality of auxiliary signals and a plurality of imaging signals collected by applying an MRI pulse sequence simultaneously to a plurality of slice locations of a subject. For each of at least one target slice location of the plurality of slice locations, the at least one processor may be configured to direct the system to generate at least one target image of the target slice location based on the plurality of auxiliary signals and the plurality of imaging signals. During the application of the MRI pulse sequence, phase modulation may be applied to at least one of the plurality of slice locations so that the plurality of slice locations have different phases during the readout of at least one of the plurality of imaging signals.

In some embodiments, the plurality of auxiliary signals may correspond to the same K-space line in K-space.

In some embodiments, for each of the at least one target slice location, the at least one processor may be configured to direct the system to determine at least one temporal basis function relating to at least one time-varying dimension of the target slice location based on the plurality of auxiliary signals. The at least one processor may be configured to direct the system to determine at least one spatial basis function relating to at least one spatial-varying dimension of the target slice location based on the at least one temporal basis function and the plurality of imaging signals. The at least one processor may be configured to direct the system to generate the at least one target image of the target slice location based on the at least one temporal basis function and the at least one spatial basis function.

In some embodiments, the at least one processor may be configured to direct the system to construct an optimization function relating to the at least one spatial basis function, and determine the at least one spatial basis function by solving the optimization function. The optimization function may incorporate the plurality of imaging signals and the at least one temporal basis function.

In some embodiments, the plurality of auxiliary signals may relate to at least one of a cardiac motion, a respiratory motion, a T1 relaxation, a T2 relaxation, a chemical exchange saturation transfer (CEST), a contrast agent dynamic, a T1ρ contrast, a molecular diffusion, or an elapsed time.

In some embodiments, the plurality of auxiliary signals and the plurality of imaging signals may be acquired by radial sampling, and the plurality of auxiliary signals may correspond to a radial line in K-space of a constant angle.

In some embodiments, the plurality of auxiliary signals and the plurality of imaging signals may be acquired by Cartesian sampling.

In some embodiments, the plurality of auxiliary signals may correspond to a Cartesian line passing through a K-space center in K-space.

In some embodiments, the phase modulation may be applied to the at least one slice location so that the at least one slice location has a random phase during the readout of each of the plurality of imaging signals.

In some embodiments, the phase modulation may be applied to the at least one slice location so that the phase of the at least one slice location alternates between a first degree and a second degree during the readout of consecutive imaging signals of the plurality of imaging signals, wherein the first degree and the second degree may be different.

In some embodiments, the first degree may be 0 degree, and the second degree may be 180 degrees.

In some embodiments, the subject may be in a free-breathing state during the application of the MRI pulse sequence.

In some embodiments, the MRI pulse sequence may include at least one excitation pulse for simultaneously exciting the plurality of slice locations of the subject.

In some embodiments, wherein the subject may include at least a portion of a heart.

According to another aspect of the present disclosure, a method for MRI is provided. The method may include obtaining a plurality of auxiliary signals and a plurality of imaging signals collected by applying an MRI pulse sequence simultaneously to a plurality of slice locations of a subject. The method may also include, for each of at least one target slice location of the plurality of slice locations, generating at least one target image of the target slice location based on the plurality of auxiliary signals and the plurality of imaging signals. During the application of the MRI pulse sequence, phase modulation may be applied to at least one of the plurality of slice locations so that the plurality of slice locations have different phases during the readout of at least one of the plurality of imaging signals.

According another aspect of the present disclosure, a non-transitory readable medium including at least one set of instructions is provided. When executed by at least one processor of a system for MRI, the at least one set of instructions may direct the at least one processor to perform a method. The method may include obtaining a plurality of auxiliary signals and a plurality of imaging signals collected by applying an MRI pulse sequence simultaneously to a plurality of slice locations of a subject. The method may also include, for each of at least one target slice location of the plurality of slice locations, generating at least one target image of the target slice location based on the plurality of auxiliary signals and the plurality of imaging signals. During the application of the MRI pulse sequence, phase modulation may be applied to at least one of the plurality of slice locations so that the plurality of slice locations have different phases during the readout of at least one of the plurality of imaging signals.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a block diagram illustrating an exemplary processing device according to some embodiments of the present disclosure;

FIG. 6 is a flowchart illustrating an exemplary process for SMS multitasking imaging according to some embodiments of the present disclosure;

FIG. 10 is a flowchart illustrating an exemplary process for generating one or more target images of a target slice location according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
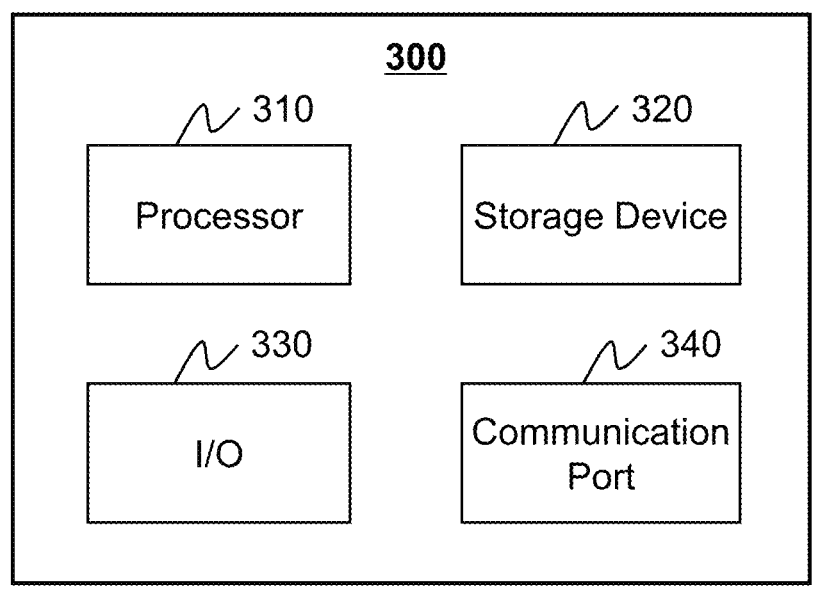
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/ units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. While the systems and methods disclosed in the present disclosure are described primarily regarding SMS multitasking imaging using an MRI system. It should be understood that this is only for illustration purposes. The systems and methods of the present disclosure may be applied to any other kind of imaging system. In some embodiments, the imaging system may include a single modality imaging system and/or a multi-modality imaging system. The single modality imaging system may include, for example, the MRI system. The multi-modality imaging system may include, for example, an X-ray imaging-magnetic resonance imaging (X-ray-MRI) system, a single photon emission computed tomography-magnetic resonance imaging (SPECT-MRI) system, a digital subtraction angiography-magnetic resonance imaging (DSA-MRI) system, a computed tomography-magnetic resonance imaging (MRI-CT) system, a positron emission tomography-magnetic resonance imaging (PET-MRI) system, etc.

An aspect of the present disclosure relates to systems and methods for MRI, more particular, to systems and methods for SMS multitasking imaging that combines the SMS technique and the multitasking technique. The SMS technique often utilizes a multiband excitation pulse to simultaneously image a plurality of slice locations of a subject, which can accelerate the scanning process. Conventionally, an additional reference scan may need to be performed to acquire reference data of each of the slice locations for slice separation. For example, reference slice images of the slice locations may be reconstructed based on the reference scan and coil sensitivity profiles of different receiver coils may be determined. A slice image of each slice location may be separated from an aliasing image acquired in SMS based on the coil sensitivity profiles. However, the additional reference scan may cause additional scan time and impair the benefit of the SMS technique.

The multitasking technique allows acquiring MRI data of a subject relating to multiple time dimensions, that is, achieving multiple tasks, via a single MRI scan of the subject. The multitasking technique may be used to conceptualize different sources of motion, relaxation, and other dynamics as different time dimensions and resolve the multiple time dimensions. By capturing, instead of avoiding the motion, relaxation, and other dynamics, the multitasking technique may efficiently perform quantitative measurement on the subject without using Electrocardiography (ECG) triggering, breath holds, etc. For example, the multitasking technique may enable non-ECG and free-breathing T1 mapping, non-ECG and free-breathing T2 mapping, and non-ECG and time-resolved T1 mapping for myocardial perfusion and dynamic contrast enhancement imaging. In other words, the multitasking technique may provide a more efficient, reliable, and comfortable imaging method for solving long-standing problems in MRI.

However, the conventional multitasking technique has a limited imaging efficiency because it collects MRI data of different slice locations separately and only a portion of the MRI data can be used in image reconstruction. For example, the multitasking technique is often used in a cardiac scan for 2D native T1 cine imaging, wherein MRI data of each single slice location of the heart of a subject is collected separately. The MRI data of a single slice location may include a plurality of auxiliary signals, which may be processed to resolve the cardiac motion and the respiratory motion. The cardiac scan lasts for a long time and has a low imaging efficiency. In typical short-axis cardiac imaging, the auxiliary signals of slice locations located at the middle or the base of the heart can provide relatively accurate motion information because the middle and the base of the heart have significant contractions and relaxations. However, since the contractions and relaxations at the slice locations near the apex are not obvious, the auxiliary signals of these slice locations have a limited accuracy and it is difficult to resolve the cardiac motion of these slice locations based on their auxiliary signals.

In order to combine the benefits of the multitasking technique and the SMS technique and address the problems of the two techniques, the present disclosure provides systems and methods for SMS multitasking imaging. Specifically, the systems and methods may obtain a plurality of auxiliary signals and a plurality of imaging signals, which may be collected by applying an MRI pulse sequence simultaneously to a plurality of slice locations of a subject (e.g., a patient). During the application of the MRI pulse sequence, phase modulation may be applied to at least one of the plurality of slice locations so that the plurality of slice locations have different phases during the readout of at least one of the plurality of imaging signals. For each of at least one target slice location of the plurality of slice locations, the systems and methods may generate at least one target image of the target slice location based on the plurality of auxiliary signals and the plurality of imaging signals.

Compared to the conventional multitasking technique, the SMS multitasking imaging technique of the present disclosure has an improved scanning efficiency (e.g., a reduced scan time) by simultaneously imaging multiple slice locations. In addition, the SMS multitasking imaging technique allows an acquisition of the auxiliary signals of multiple slice locations rather than a single slice location, which avoids the problem that auxiliary signals of a slice location at the apex have limited accuracy, and improves the data quality and the dynamic tracking based thereon. Compared to the conventional SMS technique, the SMS multitasking imaging technique disclosed herein applies phase modulation to the slice locations for slice separation, which obviates the need for an additional scan for generating reference slice images and avoids possible errors that occur in the additional scan.

Figure 1:
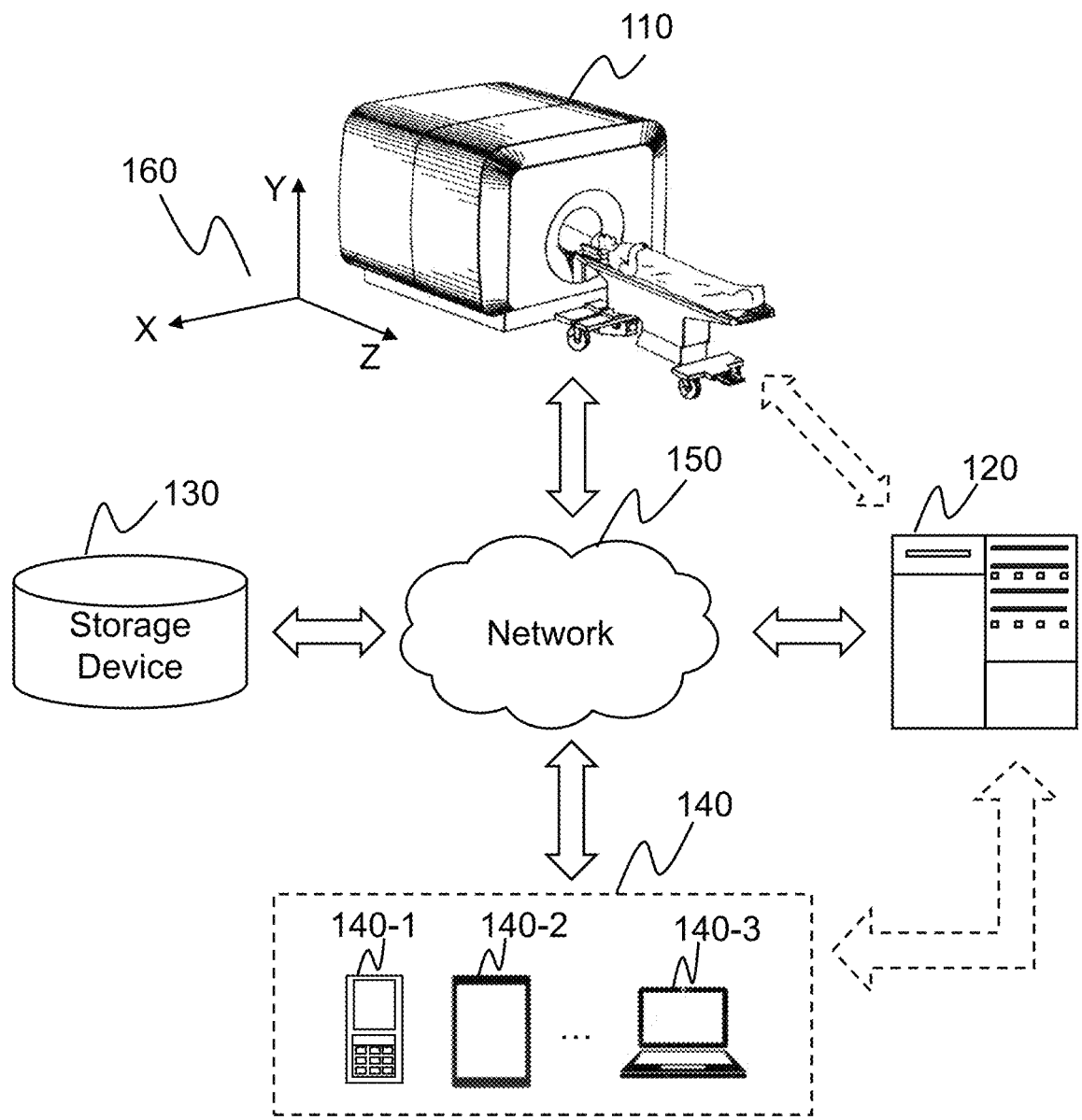
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MRI scanner 110, a processing device 120, a storage device 130, one or more terminals 140, and a network 150. In some embodiments, the MRI scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MRI scanner 110 may be connected to the processing device 120 through the network 150. As another example, the MRI scanner 110 may be connected to the processing device 120 directly.

The MRI scanner 110 may be configured to scan a subject (or a part of the subject) to acquire image data, such as echo signals (or MRI signals) associated with the subject. For example, the MRI scanner 110 may detect a plurality of echo signals by applying an MRI pulse sequence on the subject. In some embodiments, the MRI scanner 110 may include, for example, a main magnet, a gradient coil (or also referred to as a spatial encoding coil), a radio frequency (RF) coil, etc., as described in connection with FIG. 2. In some embodiments, the MRI scanner 110 may be a permanent magnet MRI scanner, a superconducting electromagnet MRI scanner, or a resistive electromagnet MRI scanner, etc., according to types of the main magnet. In some embodiments, the MRI scanner 110 may be a high-field MRI scanner, a mid-field MRI scanner, and a low-field MRI scanner, etc., according to the intensity of the magnetic field.

The subject scanned by the MRI scanner 110 may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, heart, stomach, blood vessel, soft tissue, knee, feet, or the like, or a combination thereof.

For illustration purposes, a coordinate system 160 including an X axis, a Y-axis, and a Z-axis is provided in FIG. 1. The X axis and the Z axis shown in FIG. 1 may be horizontal, and the Y-axis may be vertical. As illustrated, the positive X direction along the X axis may be from the right side to the left side of the MRI scanner 110 seen from the direction facing the front of the MRI scanner 110; the positive Y direction along the Y axis shown in FIG. 1 may be from the lower part to the upper part of the MRI scanner 110; the positive Z direction along the Z axis shown in FIG. 1 may refer to a direction in which the subject is moved out of the scanning channel (or referred to as the bore) of the MRI scanner 110.

In some embodiments, the MRI scanner 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the MRI scanner 110 may be found elsewhere in the present disclosure. See, e.g., FIG. 2 and the description thereof.

The processing device 120 may process data and/or information obtained from the MRI scanner 110, the storage device 130, and/or the terminal(s) 140. For example, the processing device 120 may obtain a plurality of auxiliary signals and a plurality of imaging signals, which are collected by applying an MRI pulse sequence simultaneously to a plurality of slice locations of a subject. As another example, for each of at least one target slice location of the plurality of slice locations, the processing device 120 may generate at least one target image of the target slice location based on the plurality of auxiliary signals and the plurality of imaging signals.

In some embodiments, the processing device 120 may be a single server or a server group. The server group may be centralized or distributed. In some embodiments, the processing device 120 may be local or remote. For example, the processing device 120 may access information and/or data from the MRI scanner 110, the storage device 130, and/or the terminal(s) 140 via the network 150. As another example, the processing device 120 may be directly connected to the MRI scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MRI scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile readand-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MRI scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable user interaction between a user and the MRI system 100. For example, the terminal(s) 140 may receive an instruction to cause the MRI scanner 110 to scan the subject from the user. As another example, the terminal(s) 140 may receive a processing result (e.g., a target image of a target slice location of the subject) from the processing device 120 and display the processing result to the user. In some embodiments, the terminal(s) 140 may be connected to and/or communicate with the MRI scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MRI scanner 110.

The network 150 may include any suitable network that can facilitate the exchange of information and/or data for the MRI system 100. In some embodiments, one or more components of the MRI system 100 (e.g., the MRI scanner 110, the processing device 120, the storage device 130, the terminal(s) 140, etc.) may communicate information and/or data with one or more other components of the MRI system 100 via the network 150. For example, the processing device 120 may obtain image data (e.g., an echo signal) from the MRI scanner 110 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MRI scanner 110. As another example, a component of the MRI system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

Figure 2:
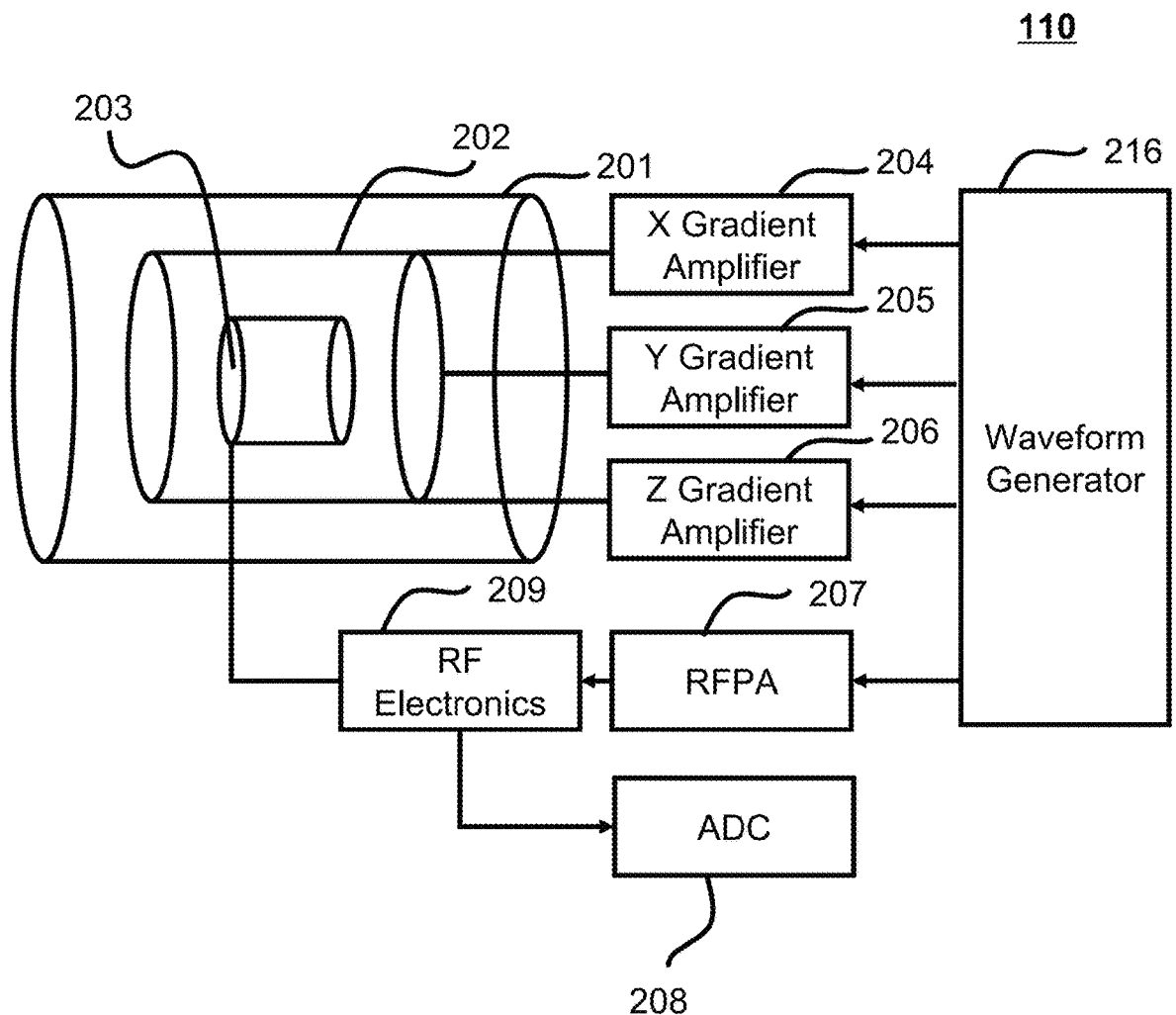
FIG. 2 is a schematic diagram illustrating an exemplary MRI scanner according to some embodiments of the present disclosure.

FIG. 2 is a schematic diagram illustrating an exemplary MRI scanner 110 according to some embodiments of the present disclosure. One or more components of the MRI scanner 110 are illustrated in FIG. 2. As illustrated, main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the subject is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI scanner 110 may further include a subject positioning system (not shown). The subject positioning system may include a subject cradle and a transport device. The subject may be placed on the subject cradle and be positioned by the transport device within the bore of the main magnet 201.

MRI systems (e.g., the MRI system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MRI image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

FIG. 3 is a schematic diagram illustrating exemplary hardware and/or software components of a computing device 300 according to some embodiments of the present disclosure. The computing device 300 may be used to implement any component of the MRI system 100 as described herein. For example, the processing device 120 and/or the terminal 140 may be implemented on the computing device 300, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 3, the computing device 300 may include a processor 310, a storage device 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data obtained from the MRI scanner 110, the terminal(s) 140, the storage device 130, and/or any other component of the MRI system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage device 320 may store data/information obtained from the MRI scanner 110, the terminal(s) 140, the storage device 130, and/or any other component of the MRI system 100. In some embodiments, the storage device 320 may include a mass storage device, a removable storage device, a volatile read-and-write memory, a read-only memory (ROM), or the like, or any combination thereof. In some embodiments, the storage device 320 may store one or more programs and/or instructions to perform exemplary methods described in the present disclosure. For example, the storage device 320 may store a program for the processing device 120 to execute for SMS multitasking imaging.

The I/O 330 may input and/or output signals, data, information, etc. In some embodiments, the I/O 330 may enable a user interaction with the processing device 120. In some embodiments, the I/O 330 may include an input device and an output device. The input device may include alpha-numeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 150) to facilitate data communications. The communication port 340 may establish connections between the processing device 120 and the MRI scanner 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
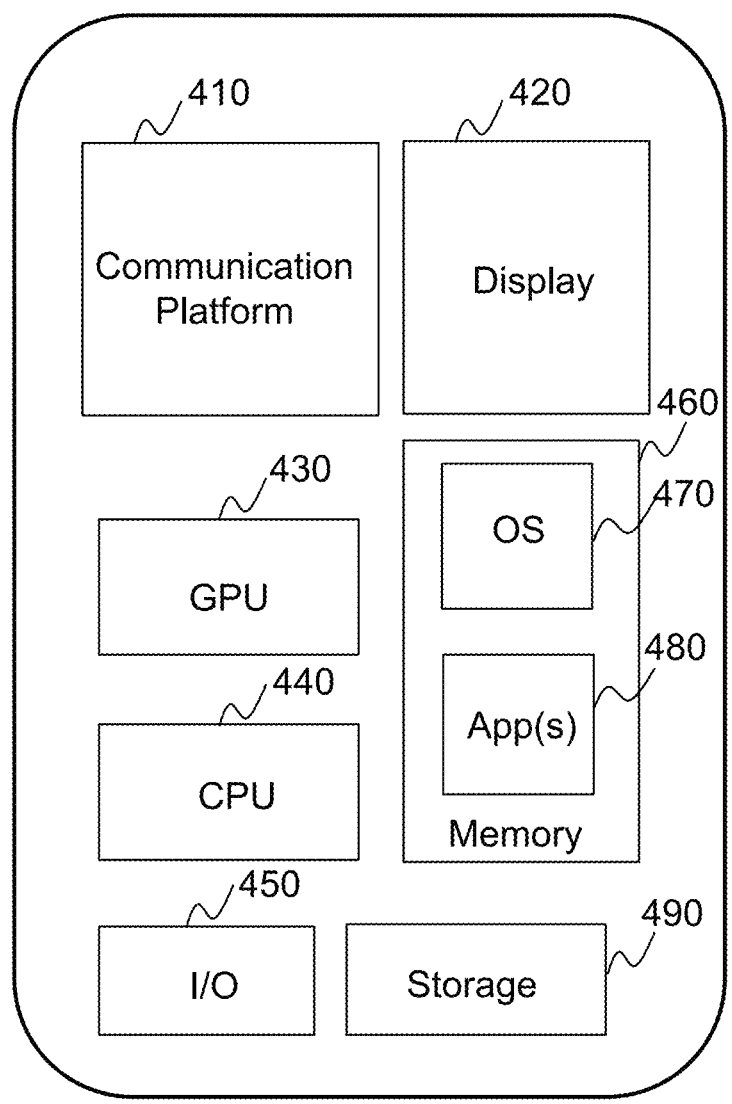
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 140 and/or the processing device 120) of the MRI system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

FIG. 5 is a block diagram illustrating an exemplary processing device 120 according to some embodiments of the present disclosure. As shown in FIG. 5, the processing device 120 may include an obtaining module 501 and a generation module 502.

The obtaining module 501 may be configured to obtain a plurality of auxiliary signals and a plurality of imaging signals, which may be collected by applying an MRI pulse sequence simultaneously to a plurality of slice locations of a subject. The auxiliary signals may include high-temporal resolution data relating to at least one time-varying dimension of the subject (or the imaged slice locations) for implementing the multitasking technique. The imaging signals may include high-spatial resolution image data relating to at least one spatial-varying dimension of the subject (or the imaged slice locations). In some embodiments, the MRI pulse sequence may be specially designed to implement both the SMS technique and the multitasking technique. More descriptions regarding the obtaining of the auxiliary signals and the imaging signals may be found elsewhere in the present disclosure. See, e.g., 601 and relevant descriptions thereof.

For each of one or more target slice locations of the slice locations, the generation module 502 may be configured to generate one or more target images of the target slice location based on the auxiliary signals and the imaging signals. The target slice location(s) may include all or a portion of the slice locations. A target image of a target slice location may include a static image and/or a dynamic image of the target slice location. In some embodiments, for each of the one or more target slice locations, the generation module 502 may determine one or more temporal basis functions relating to at least one time-varying dimension of the target slice location based on the plurality of auxiliary signals, and determine one or more spatial basis functions relating to at least one spatial-varying dimension of the target slice location based on the temporal basis function(s) and the imaging signals. The generation module 502 may further generate the one or more target images of the target slice location based on the one or more temporal basis functions and the one or more spatial basis functions. More descriptions regarding the generation of the one or more target images may be found elsewhere in the present disclosure. See, e.g., 602 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may include one or more additional modules, such as a storage module (not shown) for storing data. As another example, one or more modules of the processing device 120 described above may be omitted. Additionally or alternatively, a module of the processing device 120 may be divided into two or more units. For example, the generation module 502 may be divided into a temporal basis function determination unit, a spatial basis function determination unit, and a target image generation unit.

FIG. 6 is a flowchart illustrating an exemplary process for SMS multitasking imaging according to some embodiments of the present disclosure. In some embodiments, process 600 may be executed by the MRI system 100. For example, the process 600 may be implemented as a set of instructions (e.g., an application) stored in a storage device (e.g., the storage device 130, the storage device 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 600.

In 601, the processing device 120 (e.g., the obtaining module 501) may obtain a plurality of auxiliary signals and a plurality of imaging signals, which may be collected by applying an MRI pulse sequence simultaneously to a plurality of slice locations of a subject.

As used herein, a subject may be biological or non-biological, for example, a patient, or a specific portion, organ, tissue, and/or a physical point of the patient. Merely by way of example, the subject may include head, brain, neck, body, shoulder, arm, thorax, heart, stomach, blood vessel, soft tissue, knee, feet, or the like, or a combination thereof. In some embodiments, the subject may include at least a portion of a heart. A slice location of a subject refers to a transverse plane of the subject (e.g., a plane that is parallel to an X-Y plane defined by the coordinate system 160 as shown in FIG. 1). The count of the imaged slice locations may be equal to any positive number greater than 1, such as two, three, four, five, etc. The imaged slice locations may be located at any position of the subject. For example, the subject may include the heart of a patient, and the slice locations may include multiple slice locations located at the apex, the middle, and the base of the heart.

In some embodiments, the processing device 120 may obtain the auxiliary signals and the imaging signals from an MRI scanner. The MRI scanner may include one or more similar components to the MRI scanner 110 as described in connection with FIGS. 1 and 2. For example, the processing device 120 may direct the MRI scanner to perform an MRI scan on the subject. During the MRI scan, the MRI scanner may apply the MRI pulse sequence simultaneously to the slice locations of the subject, and collect MRI signals including the auxiliary signals and the imaging signals from the subject. The collected auxiliary signals and the imaging signals may be transmitted from the MRI scanner to the processing device 120 for further analysis. Alternatively, the collected auxiliary signals and the imaging signals may be previously collected by the MRI scanner and stored in a storage device (e.g., the storage device 130, the storage device 320, and/or the storage 490). The processing device 120 may obtain the auxiliary signals and the imaging signals from the storage device. In some embodiments, the subject may be in a free-breathing state during the MRI scan (i.e., the application of the MRI pulse sequence).

The auxiliary signals may include high-temporal resolution data relating to at least one time-varying dimension of the subject (or the imaged slice locations), which may be used to implement the multitasking technique. Exemplary time-varying dimensions may relate to a cardiac motion, a respiratory motion, a T1 relaxation, a T2 relaxation, a chemical exchange saturation transfer (CEST), a contrast agent dynamic, a T1ρ contrast, a molecular diffusion, an elapsed time, or the like, or any combination thereof. It should be noted that the exemplary time-varying dimensions are merely provided for illustration purposes, and not intended to be limiting. The at least one time-varying dimension may include any dimension that reflects time-varying characteristics or dynamic information of the subject. In some embodiments, the auxiliary signals may be used to estimate at least one temporal basis function relating to the at least one time-varying dimension, which will be described in detail in connection with FIG. 10.

In some embodiments, the auxiliary signals may correspond to the same subset of K-space (e.g., which includes one or more K-space lines) and collected by sampling the subset of K-space repeatedly with a high sampling frequency. For example, the auxiliary signals may correspond to the same K-space line in K-space and be acquired by sampling the K-space line repeatedly with a high sampling frequency. As used herein, a high sampling frequency refers to a sampling frequency that is higher than a threshold frequency. The threshold frequency may be a default value, or determined manual by a user, or determined by the processing device 120 according to data analysis. For example, the threshold frequency may be determined according to the at least one time-varying dimension to be analyzed. Merely by way of example, a time-varying dimension may relate to the respiratory motion of the subject, and the respiration cycle of the subject is close to 0.75 seconds (s). In order to capture dynamic information relating to the respiratory motion of the subject, the sampling frequency may need to be greater than a threshold frequency of 1/0.75 Hertz (HZ). As another example, the threshold frequency may be determined according to actual requirements (e.g., the accuracy requirement), experience, a data model, etc. In some embodiments, an auxiliary signal may be also referred to as a navigator signal.

The imaging signals may include high-spatial resolution image data relating to at least one spatial-varying dimension of the subject (or the imaged slice locations). Exemplary spatial-varying dimensions may relate to a slice selection direction, a phase encoding direction, a frequency encoding direction, or the like, or any combination thereof. In some embodiments, the imaging signal may be used to estimate at least one spatial basis function relating to the at least one spatial-varying dimension of the target slice location, which will be described in detail in connection with FIG. 10. In some embodiments, the imaging signals may be acquired by sampling different K-space lines in K-space.

Figure 8:
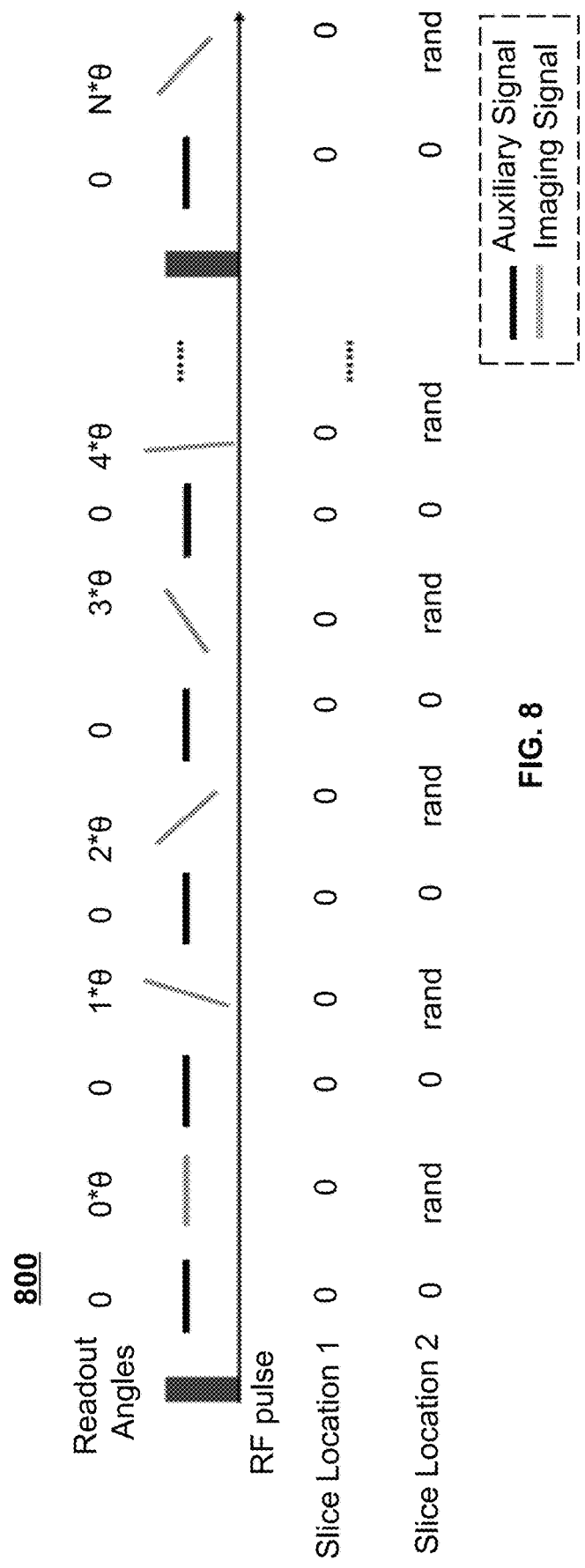
FIG. 8 is a schematic diagram illustrating an exemplary MRI pulse sequence for implementing an SMS multitasking technique according to some embodiments of the present disclosure.
Figure 9:
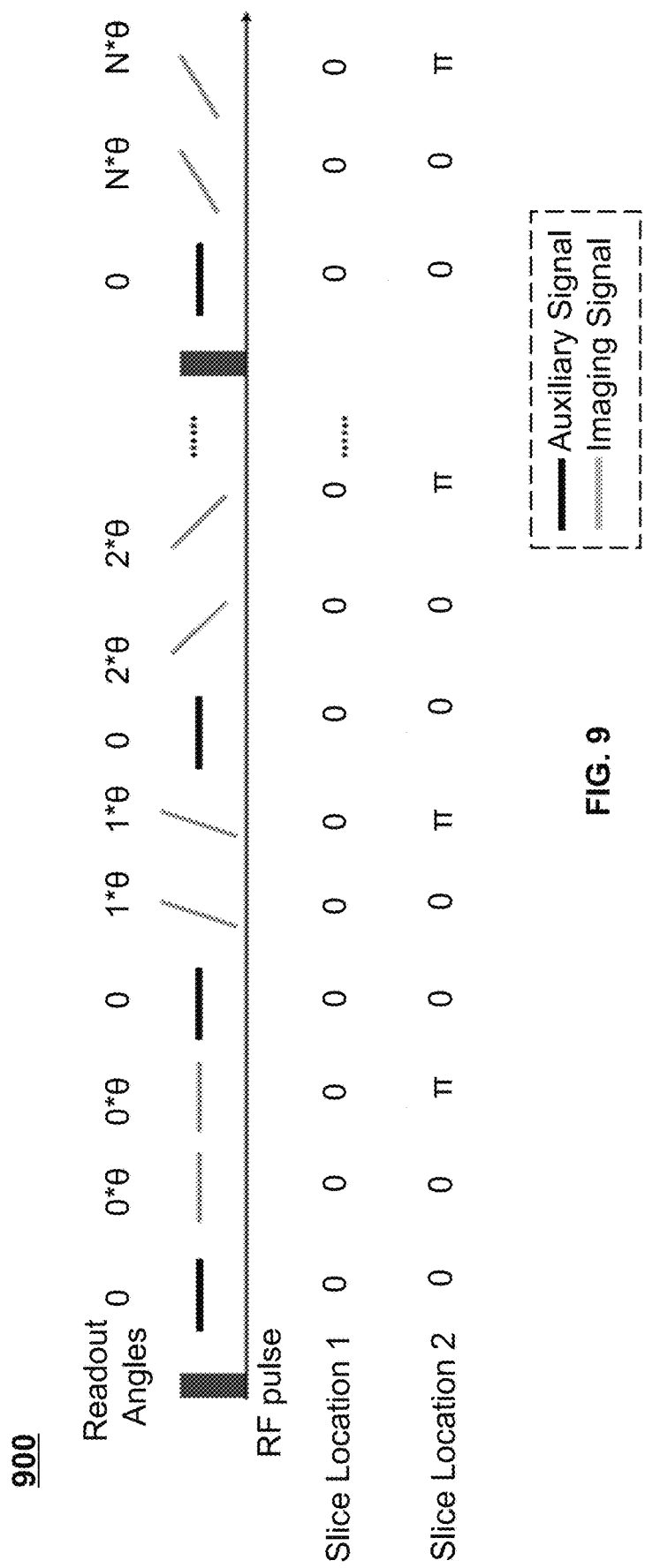
FIG. 9 is a schematic diagram illustrating another exemplary MRI pulse sequence for implementing an SMS multitasking technique according to some embodiments of the present disclosure.

The auxiliary signals and the imaging signals may be acquired by any suitable sampling pattern. In some embodiments, the auxiliary signals and the imaging signals may be acquired by radial sampling. The auxiliary signals may correspond to a radial line in K-space of a constant angle (e.g., 0°, 10°, 20°, 30°, 100°, 180°, etc.). Merely by way of example, the auxiliary signals may be acquired by sampling a radial line in the K-space of the constant angle repeatedly at a regular interval. For example, as shown in FIG. 8, a plurality of auxiliary signals may be acquired by sampling the 0° radial spoke repeatedly every odd readout. As another example, as shown in FIG. 9, a plurality of auxiliary signals may be acquired by sampling 0° radial spokes repeatedly every three readouts.

The imaging signals may correspond to a plurality of radial lines in K-space of different readout angles. In some embodiments, the processing device 120 may acquire the imaging signals by sampling the plurality of radial lines in K-space according to a golden-angle radial sampling schedule. For example, as shown in FIG. 8, the readout angles of N imaging signals are 0*θ, 1*θ, 2*θ, 3*θ, 4*θ, . . . , and N*θ, wherein N is a positive integer greater than 1 and θ refers to the golden angle about 111.25°. As another example, as shown in FIG. 9, the readout angles of the imaging signals are 0*θ, 0*θ, 1*θ, 1*θ, 2*θ, 2*θ, . . . , N*θ, and N*θ. By adopting the golden-angle radial sampling schedule, multiple radial spokes that are uniformly distributed in and cover K-space can be acquired in a relatively short time, which may improve the scanning efficiency and reduce the computation amount and the computation time. It should be understood that the imaging signals may be sampled by any other readout angles (e.g., randomly set readout angles) according to an actual need (e.g., based on the requirement(s) regarding the scanning time and/or the imaging quality).

In some embodiments, the auxiliary signals and the imaging signals may be acquired by Cartesian sampling. The auxiliary signals may correspond to the same Cartesian line in K-space, and the auxiliary signals may correspond to different Cartesian lines in K-space. In some embodiments, the auxiliary signals may correspond to the Cartesian line passing through a K-space center in K-space. In some embodiments, the imaging signals may be acquired by Cartesian sampling while the auxiliary signals may be acquired by sampling a specific radial line or spiral line in K-space repeatedly.

The auxiliary signals and the imaging signals may be acquired in any sampling order during the MRI scan of the subject. In some embodiments, the auxiliary signals and the imaging signals may be acquired interleaved during the MRI scan of the subject. For example, a first count of imaging signals may be sampled after or before every readout of a second count of auxiliary signals. The first count and the second count may be any positive integer, such as 1, 2, 3, 5, 10, etc. Merely by way of example, referring to FIG. 8, one imaging signal may be acquired after every readout of one auxiliary signal. In such cases, a ratio of the count of the imaging signals to the count of the auxiliary signals obtained in operation 601 may be 1:1. As another example, referring to FIG. 9, two imaging signals may be acquired after every readout of one auxiliary signal. In such cases, a ratio of the count of the imaging signals to the count of the auxiliary signals obtained in operation 601 may be 2:1.

In some embodiments, the first count and the second count may be set according to actual requirements, for example, a sampling frequency of the auxiliary signals needs to be greater than the threshold frequency and/or enough imaging signals need to be acquired for image reconstruction. In some embodiments, the ratio of the first count to the second count may relate to the type of the subject to be imaged. For example, to image the heart of a patient, the ratio of the first count to the second count may be equal to 1:1. As another example, to image an organ other than the heart (e.g., an arm, a knee), the ratio of the first count to the second count may be equal to 10:1.

In some embodiments, the MRI pulse sequence used to collect the auxiliary signals and the imaging signals may be of any type of MRI pulse sequences, such as a spin echo sequence, a gradient echo sequence, a diffusion sequence, an inversion recovery sequence, or another type of MRI pulse sequence as described in connection with FIG. 2, or any combination thereof. The MRI pulse sequence may be specially designed to implement both the SMS technique and the multitasking technique. As described above, to implement the multitasking technique, the auxiliary signals may be collected by sampling at least a subset of the K-space repeatedly with a high sampling frequency. To implement the SMS technique, the MRI scanner may include at least one excitation pulse (e.g., multiband RF pulse(s)) for exciting the slice locations simultaneously and a phase modulation scheme for facilitating slice separation from aliasing image data in image reconstruction.

In some embodiments, during the application of the MRI pulse sequence, phase modulation may be applied to at least one of the slice locations so that the plurality of slice locations have different phases during the readout of at least one of the plurality of imaging signals. As used herein, if at least two of the plurality of slice locations have different phases, the plurality of slice locations may be regarded as having different phases. In other words, during the readout of the at least one of the imaging signals, the phases of the slice locations may be partially or completely different from each other. In some embodiments, during the application of the MRI pulse sequence, phase modulation may be applied to each of the slice locations or a portion of the slice locations.

For example, the phase modulation may be applied to the at least one slice location so that the at least one slice location has a random phase during the readout of each of the plurality of imaging signals. As shown in FIG. 8, phase modulation may be applied to the slice location 2 so that the slice location 2 has a random phase during the readout of each of the imaging signals. As another example, the phase modulation may be applied to the at least one slice location so that the phase of the at least one slice location alternates between a first degree and a second degree during the readout of consecutive imaging signals of the plurality of imaging signals, wherein the second degree is different from the first degree. As shown in FIG. 9, phase modulation may be applied to the slice location 2 so that the phase of the slice location 2 alternates between 0 degree and 180 degrees during the readout of consecutive imaging signals of the plurality of imaging signals. As still another example, the slice locations may include three slice locations, and phase modulation may be applied to two of the three slice locations, so that the phase of one slice (e.g., a first slice) location is always 0°, the phase of one slice (e.g., a second slice) location changes from −120° to 0° to 120° periodically, and the phase of one slice (e.g., a third slice) location changes from −240° to 0° to 240° periodically. Based on the phase difference between the slice locations, the systems and methods disclosed herein may resolve the imaging signals of the slice locations easily to generate image(s) of a single slice location without performing an additional reference scan on the subject.

In some embodiments, the phase modulation may be performed via a phase modulated RF excitation pulse, a phase modulation gradient, or a combination thereof. For example, a phase modulated RF excitation pulse may be applied to excite the slice locations and modulate the phase of at least one of the slice locations. As another example, a phase modulation gradient may be applied by gradient coils (e.g., Z coils) of the MRI scanner along a slice-encoding direction after the slice locations are excited and before the readout of an imaging signal, wherein the phase modulation gradient may induce a phase difference between the slice locations for the readout of the imaging signal.

In 602, for each of one or more target slice locations of the slice locations, the processing device 120 (e.g., the generation module 502) may generate one or more target images of the target slice location based on the auxiliary signals and the imaging signals.

The target slice location(s) may include all or a portion of the slice locations. For example, the target slice location(s) may be selected from the slice locations by a user (e.g., a doctor, a technician) or according to a defaulting setting of the MRI system 100. As another example, the target slice location(s) may be selected from the slice locations by the processing device 120 according to data analysis. Merely by way of example, the target slice location(s) may include slice location(s) that undergo obvious contraction and relaxation among a plurality of cardiac slice locations.

A target image of a target slice location may include a static image and/or a dynamic image of the target slice location. In some embodiments, the static image may correspond to a specific motion phase of the subject. For example, the static image may include a slice image of a cardiac slice corresponding to a certain cardiac phase or an image of a lung slice corresponding to a certain respiratory phase. The dynamic image may reflect dynamic information of the target slice location along a time-varying dimension. In some embodiments, the dynamic image may include a series of slice images over time, such as a plurality of slice images of the target slice location corresponding to a plurality of motion phases of the subject. For example, a dynamic image may reflect the cardiac motion of a cardiac slice over a cardiac cycle, and include a plurality of images of the cardiac slice corresponding to a plurality of cardiac phases in the cardiac cycle.

In some embodiments, the processing device 120 may generate the target image(s) of a target slice location by performing process 1000 as described in connection with FIG. 10. In some embodiments, the processing device 120 may generate one or more target images of each slice location of the subject, and generate one or more target images of the subject by combining the target image(s) of each slice location. Merely by way of example, the heart of a patient may include 10 cardiac slices and the cardiac cycle of the patient may include 4 cardiac phases. The processing device 120 may generate a 2D static image corresponding to an end diastole phase for each cardiac slice based on the auxiliary signals and the imaging signals, and further generate a 3D static image of the heart of the patient corresponding to the end diastole phase by combining the 2D static images of the 10 cardiac slices. As another example, the processing device 120 may generate a dynamic image reflecting the cardiac motion in the cardiac cycle for each cardiac slice, and further generate a 4D dynamic image of the heart of the patient by combining the dynamic images of the 10 cardiac slices.

The present disclosure provides an SMS multitasking imaging technique that combines the advantages of both the SMS technique and the multitasking technique, for example, can be used to track dynamics of multiple dimensions with improved scanning efficiency. Compared to the multitasking technique, the SMS multitasking imaging technique of the present disclosure can shorten the scanning time and/or improve the accuracy of the dynamic tracking with respect to some portions that don't have obvious motion (e.g., slice locations near the apex where cardiac contractions and relaxations are not obvious). Compared to the SMS technique, the SMS multitasking imaging technique utilizes phase modulation to the slice locations for slice separation, which obviates the need for an additional scan for generating the reference image and avoids possible errors that occur in the additional scan.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, the process 600 may include an additional operation to transmit the target image(s) to a terminal device (e.g., a terminal device 140 of a doctor) for display.

Figure 7:
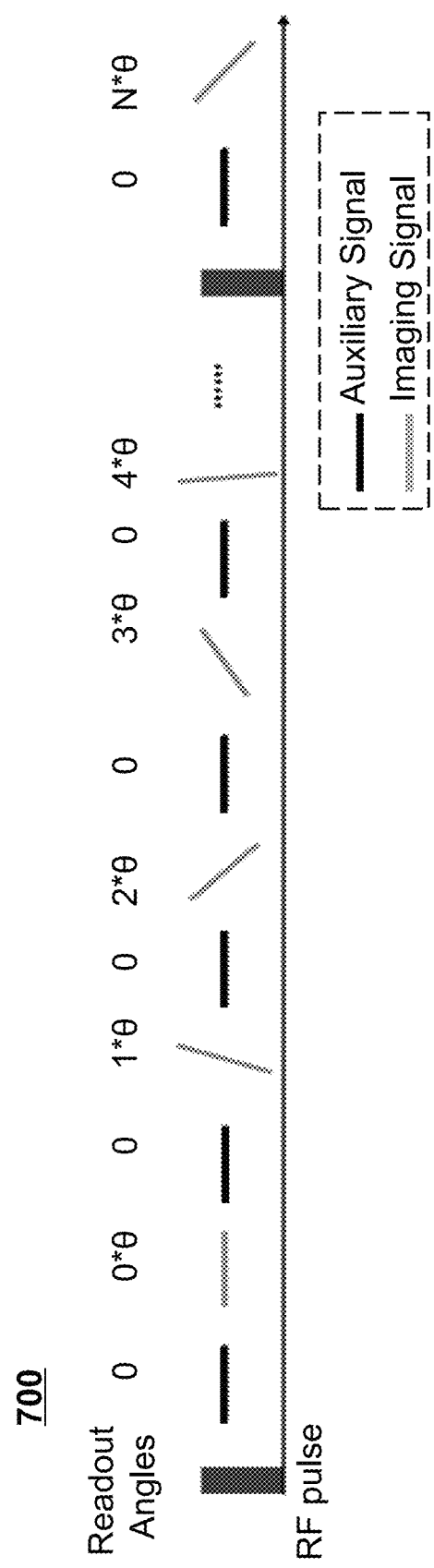
FIG. 7 is a schematic diagram illustrating an exemplary MRI pulse sequence for implementing a multitasking technique.

FIG. 7 is a schematic diagram illustrating an exemplary MRI pulse sequence 700 for implementing the multitasking technique. Conventionally, MRI signals of multiple slice locations are obtained by applying an MRI pulse sequence to each slice location of the multiple slice locations separately. For example, the MRI pulse sequence 700 may be applied by an MRI scanner (e.g., the MRI scanner 110) to a single slice location to obtain a plurality of auxiliary signals and a plurality of imaging signals of the slice location by radial sampling. As shown in FIG. 7, one imaging signal is acquired after every readout of one auxiliary signal; the auxiliary signals are obtained by sampling the 0° radial spoke repeatedly; and the imaging signals are obtained by sampling a plurality of radial lines in K-space according to a golden-angle radial sampling schedule.

FIG. 8 is a schematic diagram illustrating an exemplary MRI pulse sequence 800 for implementing the SMS multitasking technique according to some embodiments of the present disclosure. As shown in FIG. 8, the MRI pulse sequence 800 includes a plurality of excitation pulses that can simultaneously excite slice locations 1 and 2 of a subject to obtain a plurality of auxiliary signals and a plurality of imaging signals of the slice locations 1 and 2 by radial sampling. One imaging signal is acquired after every readout of one auxiliary signal, the auxiliary signals are obtained by sampling the 0° radial spoke repeatedly, and the imaging signals are obtained by sampling a plurality of radial lines in K-space according to a golden-angle radial sampling schedule. During the application of the MRI pulse sequence 800, a random phase modulation is applied to the slice location 2 such that the slice location 2 has different phases during the readout of each of the plurality of imaging signals. The phase of the slice location 1 is always equal to 0°. The slice location 2 has a random phase during the readout of each of the plurality of imaging signals.

FIG. 9 is a schematic diagram illustrating an exemplary MRI pulse sequence 900 for implementing the SMS multitasking technique according to some embodiments of the present disclosure. The MRI pulse sequence 900 may be similar to the MRI pulse sequence 800, except for certain components or features. As shown in FIG. 9, two imaging signals are acquired after every readout of one auxiliary signal, the auxiliary signals are obtained by sampling the 0° radial spokes repeatedly, and the imaging signals are obtained by sampling a plurality of radial lines in K-space according to a golden-angle radial sampling schedule. During the application of the MRI pulse sequence 900, a phase modulation scheme is applied to the slice location 2 such that the phase of the slice location 2 alternates between 0 degree and 180 degrees during the readout of consecutive imaging signals of the plurality of imaging signals. The phase of the slice location 1 is always equal to 0°.

It should be noted that the above exemplary MRI pulse sequences illustrated in FIGS. 8 and 9 and the descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the phase of a slice location may be modulated according to any other phase modulation scheme which is different from that as shown in FIGS. 8 and 9. Additionally or alternatively, the readout angle of a slice location may be different from that as shown in FIGS. 8 and 9. Moreover, the sampling order and/or the counts of the auxiliary signals and the imaging signals may be modified according to an actual need. For example, an imaging signal may be acquired by every odd readout and an auxiliary signal may be acquired by every even readout. As another example, a ratio of the count of the auxiliary signals to the count of the imaging signals may be equal to 1:5, 1:8, 1:10, or any other suitable value.

FIG. 10 is a flowchart illustrating an exemplary process for generating one or more target images of a target slice location according to some embodiments of the present disclosure. In some embodiments, process 1000 may be executed by the MRI system 100. For example, the process 1000 may be implemented as a set of instructions (e.g., an application) stored in a storage device (e.g., the storage device 130, the storage device 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 1000. In some embodiments, one or more operations of the process 1000 may be performed to achieve at least part of operation 602 as described in connection with FIG. 6.

In some embodiments, a target image of a target slice location with multiple dimensions (e.g., the spatial-varying dimension(s) and the time-varying dimension(s)) may be represented by a multi-dimensional tensor. For example, the target image may be represented as an (X+1)-way image tensor (or array), wherein the first tensor dimension may index the spatial-varying dimension(s) and each of the other X tensor dimension(s) may index a time-varying dimension. X is a positive integer and equal to the count of the time-varying dimension(s).

A low-rank tensor image model may be used to resolve multiple overlapping dynamics (e.g., the time-varying dimension(s)). For example, based on the low-rank tensor image model, the target image may be expressed by a product of a core tensor and (X+1) basis matrices. The core tensor may govern the interaction between the basis matrices. The (X+1) basis matrices may include a spatial factor matrix and X temporal factor matrix (or matrices). The spatial factor matrix may include one or more spatial basis functions relating to the spatial-varying dimension(s) of the target slice location. Each of the X temporal factor matrix (or matrices) may correspond to one of the time-varying dimension(s) and include one or more temporal basis functions relating to the corresponding time-varying dimension. In order to generate the target image, the spatial basis function(s), the temporal basis function(s) of the target slice location, and the core tensor may need to be determined based on the auxiliary signals and the imaging signals by performing the following operations.

In 1001, the processing device 120 (e.g., the generation module 502) may determine the temporal basis function(s) relating to the time-varying dimension(s) of the target slice location based on the auxiliary signals.

The determined temporal basis function(s) may include one or more temporal basis functions relating to each of the time-varying dimension(s). For example, the temporal basis function(s) may include one or more cardiac temporal basis functions relating to the cardiac motion of the subject (or the target slice location), one or more respiratory temporal basis functions relating to the respiratory motion of the subject (or the target slice location), one or more T1 recovery temporal basis functions relating to the T1 relaxation of the subject (or the target slice location), or the like, or any combination thereof. A temporal basis function relating to a time-varying dimension may reflect dynamic information along the time-varying dimension and include high-temporal resolution information.

In some embodiments, for different target slice locations, the temporal basis functions relating to a time-varying dimension may be the same if the target slice locations have the same dynamic change or similar dynamic changes along the time-varying dimension. Merely by way of example, different cardiac slices may share the same cardiac temporal basis function(s) because they follow similar laws of motion in a cardiac cycle. In such cases, operation 1001 may only need to be performed once to determine the cardiac temporal basis function(s) of the cardiac slices, and the cardiac temporal basis function(s) may be used to generate target images of different cardiac slices.

In some embodiments, the processing device 120 may determine the temporal basis function(s) of the time-varying dimension(s) and the core tensor as aforementioned based on the auxiliary signals obtained in operation 601. For example, the processing device 120 may construct a first optimization function relating to under-sampled auxiliary data (e.g., the auxiliary signals obtained in operation 601), a low-rank tensor representing full-sampled auxiliary signals to be determined, and a matrix corresponding to each time-varying dimension. The matrix corresponding to a time-varying dimension may include rows indexing the time-varying dimension and columns indexing the other time-varying dimension(s). The processing device 120 may determine the low-rank tensor representing the full-sampled auxiliary signals by solving the first optimization function. Based on the low-rank tensor, the processing device 120 may determine the temporal basis function(s) for each time-varying dimension and the core tensor. For example, the processing device 120 may utilize an explicit strategy to recover the temporal basis function(s) and the core tensor based on the low-rank tensor according to a higher order singular value decomposition (HOSVD) algorithm.

In 1002, the processing device 120 (e.g., the generation module 502) may determine the spatial basis function(s) relating to the spatial-varying dimension(s) of the target slice location based on the temporal basis function(s) and the imaging signals.

A spatial basis function of a target slice location may include high-spatial resolution information along the spatial-varying dimension(s). For example, the spatial basis function may reflect a relationship between pixel information of the target slice location in the image domain and spatial information of the target slice location in the physical domain. In some embodiments, the spatial basis function may be represented as a basis image that includes high-spatial resolution information. Different spatial basis functions may be represented as basis images that include different high-spatial resolution information.

In some embodiments, the processing device 120 may construct a second optimization function relating to the spatial basis function(s). The second optimization function may incorporate the imaging signals and the temporal basis function(s). The processing device 120 may further determine the spatial basis function(s) by solving the second optimization function. Merely by way of example, if the MRI pulse sequence 800 in FIG. 8 is used to acquire the auxiliary signals and the imaging signals of the subject, the processing device 120 may determine the spatial basis functions of the slice locations 1 and 2 according to a second optimization function shown in Equation (1) as below:

$$\hat{U}_1, \hat{U}_2 = \mathrm{argmin} \|d_{img} - \Omega F(S_1 U_1 \Phi + S_2 U_2 \Phi P)\|_2^2 + \lambda R(U_1, U_2), \quad (1)$$

where $\hat{U}_1$ represents an optimal spatial factor matrix of the slice location 1 determined by solving Equation (1), $\hat{U}_2$ represents an optimal spatial factor matrix of the slice location 2 determined by solving Equation (1), $U_1$ represents the spatial factor matrix of the slice location 1, $U_2$ represent the spatial factor matrix of the slice location 2, $d_{img}$ represents the imaging signals (i.e., the grey lines as shown in FIG. 8), $\Omega$ represents an undersampling operator, F represents a Fourier transformation operator, $S_1$ represents a coil sensitive map corresponding to the slice location 1, $S_2$ represents a coil sensitive map corresponding to the slice location 2, $\Phi$ represents the temporal basis function(s) of the slice locations 1 and 2 (e.g., in the form of one or more temporal factor matrices), P represents a random phase operator applied on the slice location 2, A represents a regularization parameter, and $\lambda R(U_1, U_2)$ represents a constraint item relating to the spatial factor matrices of the slice locations 1 and 2 (which may be omitted in some conditions). In some embodiments, $P_i = \exp(\sqrt{-1}*\theta_i)$, wherein $\theta_i$ represents a random phase applied on the slice location 2. The determined $\hat{U}_1$ and $\hat{U}_2$ may include the spatial basis function(s) of the slice location 1 and the spatial basis function(s) of the slice location 2, respectively.

As another example, if the MRI pulse sequence 900 in FIG. 9 is used to acquire the auxiliary signals and the imaging signals of the subject, the processing device 120 may determine the spatial basis functions of the slice locations 1 and 2 according to Equations (2) and (3) as below, respectively:

$$\hat{U}_1 = \text{argmin} \|(d_{img}^+ + d_{img}^-)/2 - \Omega F S_1 U_1 \Phi\|_2^2 + \lambda R(U_1), \quad (2)$$

$$\hat{U}_2 = \text{argmin} \|(d_{img}^+ + d_{img}^-)/2 - \Omega F S_2 U_2 \Phi\|_2^2 + \lambda R(U_2), \quad (3)$$

where $d_{img}^+$ represents the imaging signals acquired when the phases of the slice locations 1 and 2 are both 0°, $d_{img}^-$ represents the imaging signals acquired when the phases of the slice locations 1 and 2 are 0° and 180°, respectively.

In some embodiments, the coil sensitive maps corresponding to the slice locations 1 and 2 may be determined based on reference scans performed on the slice locations 1 and 2. For example, a reference slice image of the slice location 1 may be acquired by performing a reference scan on the slice location 1, a reference slice image of the slice location 2 may be acquired by performing a reference scan on the slice location 2, and the coil sensitive maps may be determined based on the reference slice images of the slice locations 1 and 2. In some embodiments, the coil sensitive maps corresponding to the slice locations 1 and 2 may be determined based on the imaging signals without performing a reference scan on the subject. Because of the phase modulation performed on the slice location 2, reference slice images of the slice locations 1 and 2 may be able to be generated based on the imaging signals. Merely by way of example, a first set of image data corresponding to the slice location 1 and a second set of image data corresponding to the slice location 2 may be determined based on $d_{img}^+$ and $d_{img}^-$, e.g., by performing a linear combination (e.g., addition and subtraction) on $d_{img}^+$ and $d_{img}^-$. A reference slice image of the slice location 1 may be reconstructed based on the first set of image data, a reference slice image of the slice location 2 may be reconstructed based on the second set of image data, and the coil sensitive maps may then be determined based on the reference slice images of the slice locations 1 and 2.

In 1003, the processing device 120 (e.g., the generation module 502) may generate one or more target images of the target slice location based on the temporal basis function(s) and the spatial basis function(s) of the target slice location.

As aforementioned, a target image of the target slice location with multiple dimensions may be represented by a multi-dimensional tensor, which may be determined based on the spatial factor matrix (which includes the spatial basis function(s)) of the target slice location and the temporal factor matrix (or matrices) (which include the temporal basis function(s)) of the target slice location. For example, with the temporal basis function(s) and the spatial basis function(s) available, the processing device 120 may generate the target image of the target slice location with multiple time-varying dimensions by determining a product of the temporal factor matrices of the time-varying dimensions including the temporal basis function(s), the spatial factor matrix including the spatial basis function(s), and a core tensor that governs the interaction between the temporal factor matrices and the spatial factor matrix. In some embodiments, the processing device 120 may generate a target image of the target slice location corresponding to a certain time-varying dimension based on the temporal factor matrix corresponding to the certain time-varying dimension and the spatial factor matrix including the spatial basis function(s). For example, the processing device 120 may generate a dynamic image of a cardiac slice by determining a product of a spatial factor matrix including the spatial basis function(s) of the cardiac slice, the temporal factor matrix including the temporal basis function(s) relating to the cardiac motion, and a core tensor that governs the interaction between the spatial factor matrix and the temporal factor matrix. As another example, the processing device 120 may further extract a static image of the cardiac slice corresponding to a certain cardiac phase from the dynamic image of the cardiac slice.

It should be noted that the above description regarding the process 1000 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1000 may be accomplished with one or more additional operations not described and/or without one or more of the operations discussed above. In some embodiments, the Equations provided above are illustrative examples and can be modified in various ways. For example, one or more coefficients in an Equation may be omitted, and/or the Equation may further include one or more additional coefficients.

In some embodiments, the target images of multiple target slice locations may be generated simultaneously by performing a process similar to the process 1000. The target slice locations may have the same temporal basis function(s), and the processing device 120 may determine the temporal basis function(s) of the target slice locations by performing operation 1001. The processing device 120 may also determine the spatial basis functions of the target slice locations jointly, for example, according to Equation (1) as described above. Then, for each of the target slice locations, the processing device 120 may generate the target image(s) of the target slice locations based on the temporal basis function(s) and the spatial basis function(s) of the target slice location.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, 5%, 10%, or +20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for magnetic resonance imaging (MRI), comprising:
   at least one storage device including a set of instructions; and
   at least one processor configured to communicate with the at least one storage device, wherein when executing the set of instructions, the at least one processor is configured to direct the system to perform operations including:
obtaining a plurality of auxiliary signals and a plurality of imaging signals collected by applying an MRI pulse sequence simultaneously to a plurality of slice locations of a subject, the plurality of auxiliary signals including temporal data relating to at least one time-varying dimension of the subject, the plurality of imaging signals including spatial image data relating to at least one spatial-varying dimension of the subject; and
for each of at least one target slice location of the plurality of slice locations, generating, based on the plurality of auxiliary signals and the plurality of imaging signals, at least one target image of the target slice location, wherein
during the application of the MRI pulse sequence, phase modulation is applied to at least one of the plurality of slice locations so that the plurality of slice locations have different phases during the readout of at least one of the plurality of imaging signals.

2. The system of claim 1, wherein for each of at least one target slice location of the plurality of slice locations, the generating at least one target image of the target slice location comprises:
for each of the at least one target slice location,
determining, based on the plurality of auxiliary signals, at least one temporal basis function relating to the at least one time-varying dimension of the target slice location;
determining, based on the at least one temporal basis function and the plurality of imaging signals, at least one spatial basis function relating to the at least one spatial-varying dimension of the target slice location; and
generating, based on the at least one temporal basis function and the at least one spatial basis function, the at least one target image of the target slice location.

3. The system of claim 2, wherein the determining, based on the at least one temporal basis function and the plurality of imaging signals, at least one spatial basis function relating to a spatial-varying dimension of the target slice location comprises:
constructing an optimization function relating to the at least one spatial basis function, the optimization function incorporating the plurality of imaging signals and the at least one temporal basis function; and
determining the at least one spatial basis function by solving the optimization function.

4. The system of claim 1, wherein the plurality of auxiliary signals relate to at least one of a cardiac motion, a respiratory motion, a T1 relaxation, a T2 relaxation, a chemical exchange saturation transfer (CEST), a contrast agent dynamic, a T1ρ contrast, a molecular diffusion, or an elapsed time.

5. The system of claim 1, wherein the plurality of auxiliary signals correspond to the same K-space line in K-space.

6. The system of claim 1, wherein the plurality of auxiliary signals and the plurality of imaging signals are acquired by radial sampling, and the plurality of auxiliary signals correspond to a radial line in K-space of a constant angle.

7. The system of claim 1, wherein the plurality of auxiliary signals and the plurality of imaging signals are acquired by Cartesian sampling.

8. The system of claim 7, wherein the plurality of auxiliary signals correspond to a Cartesian line passing through a K-space center in K-space.

9. The system of claim 1, wherein the phase modulation is applied to the at least one slice location so that the at least one slice location has a random phase during the readout of each of the plurality of imaging signals.

10. The system of claim 1, wherein the phase modulation is applied to the at least one slice location so that the phase of the at least one slice location alternates between a first degree and a second degree during the readout of consecutive imaging signals of the plurality of imaging signals, the second degree being different from the first degree.

11. The system of claim 10, wherein the first degree is 0 degrees, and the second degree is 180 degrees.

12. The system of claim 1, wherein the subject is in a free-breathing state during the application of the MRI pulse sequence.

13. The system of claim 1, wherein the MRI pulse sequence includes at least one excitation pulse for simultaneously exciting the plurality of slice locations of the subject.

14. The system of claim 1, wherein the subject includes at least a portion of a heart.

15. The system of claim 1, wherein the MRI pulse sequence is configured to implement both a multi-tasking technique and a simultaneous multi-slice (SMS) technique.

16. A method for magnetic resonance imaging (MRI), comprising:
obtaining a plurality of auxiliary signals and a plurality of imaging signals collected by applying an MRI pulse sequence simultaneously to a plurality of slice locations of a subject, the plurality of auxiliary signals including temporal data relating to at least one time-varying dimension of the subject, the plurality of imaging signals including spatial image data relating to at least one spatial-varying dimension of the subject; and
for each of at least one target slice location of the plurality of slice locations, generating, based on the plurality of auxiliary signals and the plurality of imaging signals, at least one target image of the target slice location, wherein
during the application of the MRI pulse sequence, phase modulation is applied to at least one of the plurality of slice locations so that the plurality of slice locations have different phases during the readout of at least one of the plurality of imaging signals.

17. The method of claim 16, wherein for each of at least one target slice location of the plurality of slice locations, the generating at least one target image of the target slice location comprises:
for each of the at least one target slice location,
determining, based on the plurality of auxiliary signals, at least one temporal basis function relating to the at least one time-varying dimension of the target slice location;
determining, based on the at least one temporal basis function and the plurality of imaging signals, at least one spatial basis function relating to the at least one spatial-varying dimension of the target slice location; and
generating, based on the at least one temporal basis function and the at least one spatial basis function, the at least one target image of the target slice location.

18. The method of claim 17, wherein the determining, based on the at least one temporal basis function and the plurality of imaging signals, at least one spatial basis function relating to a spatial-varying dimension of the target slice location comprises:
    constructing an optimization function relating to the at least one spatial basis function, the optimization function incorporating the plurality of imaging signals and the at least one temporal basis function; and
    determining the at least one spatial basis function by solving the optimization function.

19. The method of claim 16, wherein the plurality of auxiliary signals relate to at least one of a cardiac motion, a respiratory motion, a T1 relaxation, a T2 relaxation, a chemical exchange saturation transfer (CEST), a contrast agent dynamic, a T1p contrast, a molecular diffusion, or an elapsed time.

20. A non-transitory readable medium, comprising at least one set of instructions, wherein when executed by at least one processor of a system for magnetic resonance imaging (MRI), the at least one set of instructions directs the at least one processor to perform a method, the method comprising:
    obtaining a plurality of auxiliary signals and a plurality of imaging signals collected by applying an MRI pulse sequence simultaneously to a plurality of slice locations of a subject, the plurality of auxiliary signals including temporal data relating to at least one time-varying dimension of the subject, the plurality of imaging signals including spatial image data relating to at least one spatial-varying dimension of the subject; and
    for each of at least one target slice location of the plurality of slice locations, generating, based on the plurality of auxiliary signals and the plurality of imaging signals, at least one target image of the target slice location, wherein
        during the application of the MRI pulse sequence, phase modulation is applied to at least one of the plurality of slice locations so that the plurality of slice locations have different phases during the readout of at least one of the plurality of imaging signals.

* * * * *